(12) United States Patent
Heyer et al.

(10) Patent No.: US 7,622,630 B2
(45) Date of Patent: Nov. 24, 2009

(54) CHIMERIC CANCER MODELS

(75) Inventors: Joerg Heyer, Cambridge, MA (US); Murray Robinson, Boston, MA (US); William Rideout, III, Cambridge, MA (US); Ronald Depinho, Brookline, MA (US); Steven C. Clark, Winchester, MA (US); Yinghui Zhou, Belmont, MA (US); Tyler Jacks, West Newton, MA (US); Ronan C. O'Hagan, Arlington, MA (US)

(73) Assignee: AVEO Pharmaceuticals, Inc., Cambridge, MA (US)

( * ) Notice: Subject to any disclaimer, the term of this patent is extended or adjusted under 35 U.S.C. 154(b) by 117 days.

(21) Appl. No.: 10/570,116

(22) PCT Filed: Aug. 27, 2004

(86) PCT No.: PCT/US2004/028098

§ 371 (c)(1),
(2), (4) Date: Jun. 1, 2007

(87) PCT Pub. No.: WO2005/020683

PCT Pub. Date: Mar. 10, 2005

(65) Prior Publication Data

US 2007/0292948 A1 Dec. 20, 2007

Related U.S. Application Data

(60) Provisional application No. 60/499,277, filed on Aug. 28, 2003, provisional application No. 60/518,249, filed on Nov. 7, 2003.

(51) Int. Cl.
C12N 15/00 (2006.01)
A01K 67/00 (2006.01)
C12N 5/06 (2006.01)

(52) U.S. Cl. ............................. 800/25; 800/10; 800/18; 435/354

(58) Field of Classification Search ................... 800/21, 800/25, 3, 10; 435/354
See application file for complete search history.

(56) References Cited

FOREIGN PATENT DOCUMENTS

WO WO 01/09308 2/2001

OTHER PUBLICATIONS

Wheeler Theriogenology. 2001, (56), 1345-1369.*
Prell et al, Anat. Histol. Embryol. 2002, vol. 31, 169-186.*
Niemann et al Rev. Sci, Tech. Off. Int. Spiz. 2005, (24), 285-298.*
Smith Journal of Biotechnology, 99:1-22, 2002.*
McGovern Br Vet J. 1976 Jan.-Feb.; 132(1): 68-75.*
James et al Dev Biol. Jul. 1, 2006;295(1):90-102.*
Anderson Biol Reprod. 1988; 38(1): 1-15.*
Serrano et al Cell, 1996, 85, 27-37.*
Eggan et al., "Male and female mice derived from the same embryonic stem cell clone by tetraploid embryo complementation," *Nature Biotechnology*, 20: 455-459 (2002).
Seibler et al., "Rapid generation of inducible mouse mutants," *Nucleic Acids Research*, 31: e12 1-8 (2003).
Bockamp et al., 2002, "Of mice and models: improved animal models for biomedical research," *Physiological Genomics*,11:115-132.
Chin et al., 2000, "Flipping the oncogene switch illumination of tumor maintenance and regression," *Trends in Genetics*,16:147-150.
Chin et al., 1999, "Essential role for oncogenic ras in tumor maintenance," *Nature*, 400:468-472.
Cichowski et al., 1999, "Mouse models of tumor development in neurofibromatosis Type 1," *Science*, 286:2172-2176.
Ding et al., 2001, "Mouse astrocytoma models: embryonic stem cell mediated transgenesis," *Journal of Neuro-Oncology*, 53:289-296.
Ding et al., 2001, "Astrocyte-specific expression of activated p21-ras results in malignant astrocytoma formation in a transgenic mouse model of human gliomas," *Cancer Research*, 61:3826-3836.
Era et al., 2000, "Regulated expression of P210 Bcr-Abl during embryonic stem cell differentiation stimulates multipotential progenitor expansion and myeloid cell fate," *Proc, Nat'l Academy of Sciences (USA)*, 97:1737-1742.
Fisher et al, 1999, "Development of a flexible and specific gene delivery system for production of murine tumor models," *Oncogene*, 18:5253-5260.
Fisher et al., 2001, "Induction and apoptotic regression of lung adenocarcinomas by regulation of a K-ras transgene in the presence and absence of tumor suppressor genes," *Genes & Development*, 15:3249-3262.
Herzig et al., 2002, "Recent advances in cancer research: mouse models of tumorigenesis," *Biochimica et Biophysica Acta*,1602:97-113.

(Continued)

Primary Examiner—Deborah Crouch
Assistant Examiner—Anoop Singh
(74) Attorney, Agent, or Firm—Gary L. Creason

(57) ABSTRACT

Chimeric nonhuman mammals useful as inducible spontaneous cancer models are disclosed. The nonhuman mammals are obtained by introducing one or more genetically modified embryonic stem (ES) cells into an early stage embryo, and then implanting the manipulated embryo into a surrogate mother. The ES cells contain a recombinant oncogene, and also may contain a genetic mutation that deletes or inactivates a tumor suppressor gene. Models of different types of cancer are produced by introducing different combinations of genetic mutations into the ES cells that are introduced into the early stage embryo.

6 Claims, 2 Drawing Sheets

OTHER PUBLICATIONS

Jackson-Grusby, 2002, "Modeling cancer in mice," *Oncogene*, 21:5504-5514.

Johnson et al., 2001, "Somatic activation of the K-ras oncogene causes early onset lung cancer in mice," *Nature*, 410:1111-1116.

Robanus-Maandag et al., 1998, "p107 is a suppressor of retinoblastoma development in pRb-deficient mice," *Genes & Development*, 12:1599-1609.

Smith-Arica et al., 2000, "Cell type specific and regulatable transgenesis in the adult brain: adenovirus-encoded combined transcriptional targeting and inducible transgene expression," *Molecular Therapy*, 2:579-587.

Van Dyke et al., 2002, "Cancer modeling in the modern era: progress and challenges," *Cell*, 108:135-144.

* cited by examiner

US 7,622,630 B2

CHIMERIC CANCER MODELS

This application is a national stage filing under 35 U.S.C. § 371 of International Application No. PCT/US2004/028098, filed Aug. 27, 2004, which claims benefit under 35 U.S.C. §119(e) of U.S. Provisional Application No. 60/499,277, filed Aug. 28, 2003 and U.S. Provisional Application No. 60/518,249, filed Nov. 7, 2003, the disclosures of each of which are hereby incorporated-by-reference herein in its entirety.

BACKGROUND OF THE INVENTION

Transgenic and knockout technologies have made possible simulation of human genetic mutations in laboratory animals such as mice. However, it is a time-consuming process to generate complex disease models containing multiple genetic mutations due to the need for mating various animal strains to obtain the desired allele combinations in one animal. There is a need for rapid production of animals that harbor multiple genetic mutations in a substantial number of their cells and so as to be prone to diseases such as cancer.

SUMMARY OF THE INVENTION

It has been discovered that it is possible to make more than two genetic alterations in a nonhuman mammalian embryonic stem (ES) cell while maintaining the pluripotency of the ES cell. In addition, it has been discovered that when embryonic stem cells containing a recombinant oncogene are injected into an early stage embryo, the resulting chimeric mammal is a useful in vivo cancer model. Such chimeric animals of the invention provide certain advantages over conventional transgenic animals that contain the same genetic modification(s) present in the genetically modified cells of the chimeric animal.

Based in part on these discoveries, the invention provides a chimeric nonhuman mammal, some of whose cells, but not all of whose cells, contain a recombinant oncogene. In some embodiments of the invention, the recombinant oncogene, e.g., an activated oncogene, is operably linked to an inducible promoter. In some embodiments of the invention, the cells containing a recombinant oncogene also contain a genetic mutation that causes the mammal to have greater susceptibility to cancer than a mammal not containing the genetic mutation. In preferred embodiments of the invention the nonhuman mammal is a mouse.

Examples of recombinant oncogenes useful in mammals of the invention include HER2, K-RAS, and EGFR. An example of a genetic mutation useful for causing the mammal to have an increased susceptibility to cancer is a mutation that deletes or inactivates a tumor suppressor gene. Examples of tumor suppressor genes that can be deleted or inactivated in mammals of the invention are Ink4a, P53 and PTEN. In some embodiments of the invention, the inducible promoter includes a response element whose activity depends on a transactivator encoded by a transactivator gene operably linked to a tissue specific promoter. An example of such an inducible promoter is a TetO (tetracycline operator) promoter.

The invention provides a nonhuman mammalian ES cell containing a genome comprising a recombinant oncogene operably linked to an inducible promoter; and a genetic mutation that causes a mammal containing cells descended from the ES cell to have greater susceptibility to cancer than a mammal not containing cells descended from the ES cell. In preferred embodiments of the invention, the ES cell is a mouse ES cell.

The invention also provides differentiated cells derived from an ES cell of the invention, and cancer cells derived from an ES cell of the invention.

The invention provides a method for obtaining a chimeric nonhuman mammal, some of whose cells, but not all of whose cells, contain a genome comprising: (a) a recombinant oncogene operably linked to an inducible promoter; and (b) a genetic mutation that causes the mammal to have greater susceptibility to cancer than a mammal not containing the genetic mutation. The method includes: (a) providing a nonhuman mammalian ES cell containing a genome comprising a recombinant oncogene operably linked to an inducible promoter; and a genetic mutation that causes a mammal containing cells descended from the ES cell to have greater susceptibility to cancer than a mammal not containing cells descended from the ES cell; (b) introducing the ES cell into a host nonhuman mammalian embryo, e.g., by injection, thereby producing a manipulated embryo, and (c) implanting the manipulated embryo into a surrogate mother.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting. Throughout this specification and claims, the word "comprise," or variations such as "comprises" or "comprising" will be understood to imply the inclusion of a stated integer or group of integers but not the exclusion of any other integer or group of integers. Other features and advantages of the invention are described in the following detailed description.

DETAILED DESCRIPTION OF THE INVENTION

Figure 1:
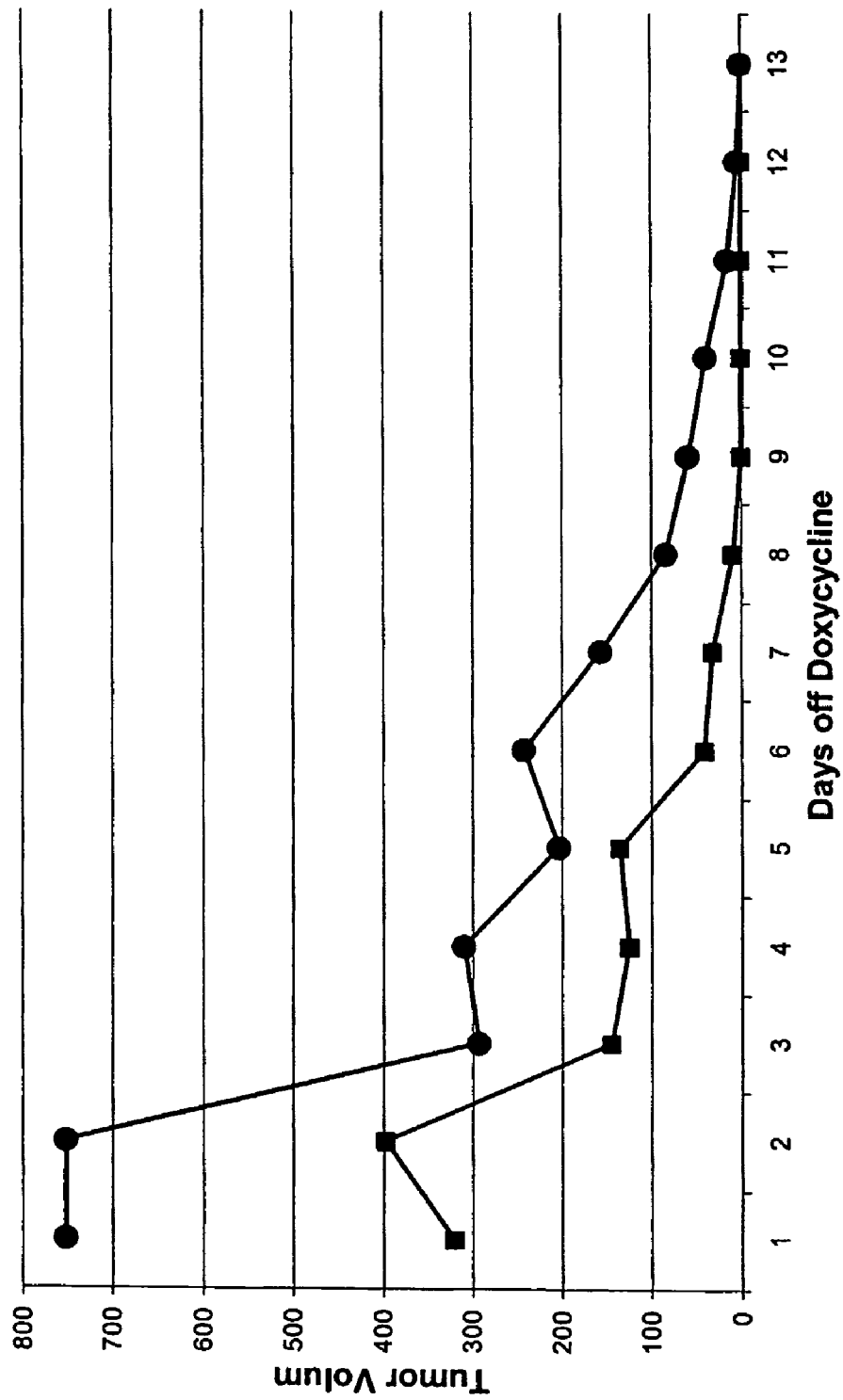
FIG. 1 is a graph of data showing the regression of two tumors from a breast Her2 model mouse (mouse #259) after doxycycline withdrawal from the drinking water. Squares represent the tumor that arose in the left fourth mammary gland. Circles represent the tumor that arose in the right fourth mammary gland. The mouse had been on doxycycline for 6 weeks. Day 1 represents the first measurement of the tumors. After measuring the tumor size, doxycycline was withdrawn from the drinking water. Tumors were measured every day for two weeks. Doxycycline withdrawal resulted in complete regression of the tumors.

This invention features methods of studying the role of a given protein in disease development (e.g., tumor development), the context-dependent oncogenicity of a genetic mutation, the toxicity of a given protein in organ development (including survival). The invention also features cells useful in these methods, e.g., ES cells having more than two (e.g., three, four, five, six, seven or eight) recombinant (i.e., not naturally occurring) genetic alterations in their genomes. This invention also features a chimeric nonhuman mammal some of whose cells differ genetically from other cells in the mammal and derive from such ES cells. This animal is produced from a multicellular, early-stage embryo, e.g., a blastocyst, into which the ES cells are injected. In preferred embodiments, the chimeric animal is disease-prone and develops a disease such as cancer. When the ES cells and the blastocyst into which they are injected are derived from the same animal strain, the chimeric mammal is also called a mosaic mammal. In addition to the above ES cell injection method, a mosaic animal also can be developed from an embryo that has been infected with viral constructs containing the desired genetic elements.

While preserving the same genetic design as a germline transgenic model, the chimeric model of this invention provides new advantages for studying diseases involving multiple genes. The chimeric model has significantly improved the speed and flexibility of disease model development. For example, to generate a transgenic melanoma model described in Chin et al., Nature 400:468-472 (1999), one would have to breed three animal lines with four respective genetic alterations—a homozygous INK4a null mutation (i.e., null mutations on both INK4a alleles), a Tyr-rtTA transgene, and a tetO-H-ras transgene—to obtain a transgenic animal with all four genetic alterations. This requires a large amount of time. In contrast, a chimeric melanoma model of this invention requires no breeding. One only needs to establish ES cells with all four genetic alterations and inject them into a blastocyst, which develops into an intact animal upon transplantation into the uterus of a surrogate mother. The average time saved can be as much as one year. To establish animal models for a different disease, one needs only to introduce into ES cells different sets or combinations of genetic mutations.

The chimeric model of this invention further allows the study of genes important in early development, because the chimeric model provides qualitative correlation between the degree of chimerism and animal viability. The chimeric model also provides a vehicle for testing anti-cancer therapeutics.

The present invention has overcome a major hurdle in ES cell technology. Before this invention, it was widely believed that ES cells subjected to more than two genetic alterations through recombinant DNA technology were prone to differentiation and loss of pluripotency.

I. Genetically altered ES cells

An ES cell line of this invention contains more than two recombinant genetic alterations in its genome. The ES cell line can be established by introducing more than two nucleic acid constructs into an ES cell concurrently or sequentially, where each construct may contain one or more genetic elements that will cause genetic alterations of the host genome. These genetic elements can also be inserted into one single vector, e.g., a BAC, PAC, YAC or MAC vector.

Exemplary genetic elements include oncogenes, RNA interference constructs, selectable marker genes (e.g., drug selection marker genes and genes encoding fluorescent or luminescent proteins), and knockout constructs targeting an endogenous disease-preventing gene (e.g., tumor suppressor genes). A desired genetic element can be incorporated into the genome randomly or at a targeted location.

Targeted genetic alterations can introduce a desired change to a specific location in an endogenous gene involved in a genetic disease, such as neurodegenerative diseases (e.g., the APP gene in Alzheimer's disease and the SOD-1 gene in Lou Gehrig's disease), heart diseases (e.g., the TBX-1 or -5 gene in heart diseases and Velo-Cardio-Facial Syndrome), diabetes (e.g., the AKT gene in Type II), and autoimmune diseases. Examples of the changes include a null (knock out) mutation to a tumor suppressor gene or an activating mutation (knock in) to a cellular oncogene. For instance, one can replace a coding or regulatory region of a tumor suppressor gene with a selectable marker gene flanked by a pair of LoxP sites; or insert a dominant negative mutation into a tumor suppressor gene; or replace the native promoter of a cellular oncogene with a constitutive or inducible promoter; or inserting an activating mutation into a cellular oncogene (see, e.g., Johnson et al., Nature 410:1111-6 (2001)). Such a genetic alteration can be accomplished by homologous recombination. In a nucleic acid construct used for homologous recombination, the genetic alteration to be introduced into the host genome is flanked by sequences homologous to the targeted genomic region.

Oncogenes useful in establishing the chimeric disease model of this invention include, without limitation, those encoding K-RAS, H-RAS, N-RAS, epidermal growth factor receptor (EGFR), MDM2, TGF-β, RhoC, AKT family members, myc (e.g., c-myc), β-catenin, PDGF, C-MET, PI3K-CA, CDK4, cyclin B1, cycline D1, estrogen receptor gene, progesterone receptor gene, Her2 (also known as neu or ErbB2), other ErbB genes (including ErbB1, ErbB3, and ErbB4), genes in the MAPK and PI3K-AKT signal transduction pathways, TGFα, ras-GAP, Shc, Nck, Src, Yes, Fyn, Wnt, and Bcl2 anti-apoptotic family members (e.g., Bcl2) as well as their activated forms, and viral proteins such as PyV MT and SV40 T antigens. Activating mutations of these oncogenes (e.g., Her2V664E, K-RasG12D, and β-cateninΔ131) can also be used.

Tumor suppressor genes whose inactivation is useful in establishing the chimeric disease model include, without limitation, Rb, P53, INK4a, PTEN, LATS, Apafl, Caspase 8, APC, DPC4, KLF6, GSTP1, ELAC2/HPC2 or NKX3.1. Other examples of tumor suppressor genes are those involved in DNA damage repair (e.g., ATM, CHK2, ATR, BRCA1, BRCA2, MSH2, MSH6, PMS2, Ku70, Ku80, DNA/PK, XRCC4 or MLH1), and cell signaling and differentiation (e.g., Neurofibromatosis Type 1, Neurofibromatosis Type 2, Adenomatous Polyposis Coli, the Wilms tumor-suppressor protein, Patched or FHIT). In addition to targeted mutation, tumor suppressor genes (or any other disease-preventing genes) can be inactivated by an antisense RNA, RNA interference (RNAi), or ribozyme agent expressed from a construct stably integrated into the host genome.

In some embodiments of this invention, the chimeric disease model is developed from ES cells that contain an introduced active oncogene as well as one or more inactivated endogenous tumor suppressor gene(s). For example, the ES cells can contain genetic alterations that result in the expression of an activated form of EGFR (designated as EGFR*) in combination with reduced $p16^{INK4a}$ or $p19^{ARF}$ expression (e.g., genetic alterations that produce an EGFR*+ and INK4a/ARF$^{-/-}$ genotype); genetic alterations that result in PDGF expression in combination with reduced p53 expression (e.g., genetic alterations that produce a PDGF+ and p53$^{-/-}$ genotype); genetic alterations that result in TGF-α expression in combination with reduced p53 expression (e.g., genetic alterations that produce a TGFα+ and p53$^{-/-}$ genotype); and genetic alterations that result in reduced PTEN expression and reduced $p16^{INK4a}$ or $p19^{ARF}$ expression (e.g., genetic alterations that produce a $PTEN^{-/-}$ and $INK4a/ARF^{-/-}$ genotype).

An example of suitable set of genetic modifications for production of a lung cancer model is TetO-EGFR* CCSP-rtTA, $p53^{-/-}$, TetO-luciferase and PGK-puromycin (selectable antibiotic resistance marker). An example of a suitable set of genetic modifications for production of a colon cancer model is TetO-K-RAS, villin-rtTA, $APC^{-/-}$, TetO-luciferase and PGK-puromycin. An example of a suitable set of genetic modifications for production of a glioblastoma cancer model is TetO-EGFR*, Nestin-rtTA, $p53^{-/-}$, TetO-luciferase and PGK-puromycin. An example of a suitable set of genetic modifications for production of a prostate cancer model is TetO-AKT1, probasin-rtTA, $Rb^{-/-}$, TetO-luciferase and PGK-puromycin. An example of a suitable set of genetic modifications for production of a liver cancer model is TetO-β, catenin, ApoE-rtTA, $NF1^{-/-}$, TetO-luciferase and PGK-puromycin.

Various vectors can be used to make the nucleic acid constructs for this invention. These vectors can be based on plasmids or viruses such as retroviruses, adenoviruses, and lentiviruses. The vectors can be introduced into ES cells via a variety of methods, including but not limited to, cell fusion (e.g., spheroplast fusion), liposome fusion (transposomes), conventional nucleic acid transfection methods (such as calcium phosphate precipitation, electroporation, microinjection), and infection by viral vectors. A variety of methods can be used to screen for ES cells that have stably incorporated the desired genetic alterations. Such methods include, without limitation, detection of drug resistance where a drug selection marker gene (e.g., a neomycin-resistant gene, a puromycin-resistant gene, or a hygromycin-resistant gene) is co-introduced; detection of fluorescence/bioluminescence emission where a fluorescent/bioluminescent marker gene (e.g., a gene encoding a green, yellow, blue or red fluorescent protein, and Luciferase genes) is co-introduced; polymerase chain reaction ("PCR"); and Southern blot analysis.

The ES cells can be genetically altered to contain a nucleic acid sequence that is regulated in an inducible manner. For example, an introduced oncogene or RNA interference sequence can be placed under the control of an inducible promoter such as the tetracycline-regulated promoter system described in e.g., WO 01/09308. In this case, administering the inducing agent (e.g., tetracycline or doxycycline) via food or drinking water to a chimeric animal, in which at least some cells originate from these genetically altered ES cells, can result in expression of the oncogene or RNAi product. Other inducible promoters include, without limitation, a metallothionine promoter, the IPTG/lacI promoter system, the ecdysone promoter system, and the "lox stop lox" system for irreversibly deleting inhibitory sequences for translation or transcription. Instead of inducible promoters, the expression of a disease-causing gene can also be inducibly switched on or off by fusing the gene's polypeptide product to, e.g., an estrogen receptor polypeptide sequence, where administration of estrogen or an estrogen analog (e.g., hydroxytamoxifen) will allow the correct folding of the polypeptide into a functional protein.

The introduced polypeptide-encoding or interfering RNA-encoding sequence can also be placed under a general, constitutively active promoter, e.g., a cytomegalovirus (CMV) promoter, EF1α, retroviral LTRs, and SV40 early region. Alternatively, the coding sequence can be placed under the control of a tissue-specific promoter, such as a tyrosinase promoter or a TRP2 promoter in the case of melanoma cells and melanocytes; an MMTV or WAP promoter in the case of breast cells and/or cancers; a Villin or FABP promoter in the case of intestinal cells and/or cancers; a PDX promoter in the case of pancreatic cells; a RIP promoter in the case of pancreatic beta cells; a Keratin promoter in the case of keratinocytes; a Probasin promoter in the case of prostatic epithelium; a Nestin or GFAP promoter in the case of central nervous system (CNS) cells and/or cancers; a Tyrosine Hydroxylase, S100 promoter or neurofilament promoter in the case of neurons; the pancreas-specific promoter described in Edlund et al. Science 230:912-916 (1985); a Clara cell secretory protein promoter in the case of lung cancer; and an Alpha myosin promoter in the case of cardiac cells.

Developmentally regulated promoters may also be selected. They include, without limitation, the murine hox promoters (Kessel and Gruss, Science 249:374-379 (1990)) and the α-fetoprotein promoter (Campes and Tilghman, Genes Dev. 3:537-546 (1989)).

Any ES cell lines that provide adequate chimerism can be used in this invention. The cell lines include, without limitation, E14.1, WW6, CCE, J1, and AB1. See also Alex Joyner, Ed., Gene Targeting, A Practical Approach, Chapter 4 (Virginia Papaioannou), Oxford Press, $2^{nd}$ Ed., (2000). In some embodiments, the ES cell lines provide 10% or higher chimerism. In some embodiments, the ES cell lines provide 90% or higher chimerism.

II. Chimeric Nonhuman Animals

As used herein, "chimeric" means chimeric in terms of ontogeny. Accordingly, a chimeric nonhuman mammal is an animal that has grown, i.e., developed, directly from a multicellular embryo into which at least one genetically modified ES cell has been injected or aggregated. A chimeric nonhuman mammal of the invention is to be distinguished from a morphologically developed animal that has received a xenograft, e.g., an organ graft, a tissue graft, or a tumor graft from another animal.

As used herein, "nonhuman mammal" means any mammal other than a human, e.g. a rat, a mouse, a hamster or a guinea pig.

A chimeric nonhuman mammal of the invention can be generated by introducing ES cells containing into a host embryo. This can be done, for example, by blastocyst injection or aggregation with earlier stage pre-implantation embryos (e.g., eight-cell embryo). The embryo is subsequently transferred into a surrogate mother for gestation. Chimerism in the born animal can be determined by phenotype (such as fur color, if the host embryo and the ES cells are derived from animal strains of different fur colors), PCR, Southern blot analysis, or biochemical or molecular analysis of polymorphic genes (such as glucose phosphate isomerase). To facilitate identification of chimeric animals having a desired genetic alteration, one can co-introduce a detectable reporter gene and the desired genetic alteration into the ES cells. Exemplary reporter genes include those that encode a fluorescent protein such as a green fluorescent protein, a yellow fluorescent protein, a blue fluorescent protein, or a luminescent protein such as luciferase or β-galactosidase.

To increase the contribution of introduced ES cells to a specific tissue, one can use a host embryo that is deficient in generating that issue. This can be accomplished by any suitable method, including inducible expression of a toxin gene, e.g., diphtheria toxin, in a specific cell type, or tissue-specific deletion of genes needed for generating this cell type. In such a complementation system, all or most of the cells of the desired cell type or tissue will be derived from the introduced ES cells.

In some embodiments of the invention, the nonhuman mammals are immunocompromised or immunodeficient. Diseases may develop sooner and/or faster in such animals. To develop such animals, one can use blastocysts derived from, for example, an X-linked SCID animal, or a RAG1−/− or RAG2−/− animal.

The chimeric animals of this invention provide efficient models to develop diseases that originate from introduced ES cells. In an inducible cancer model of this invention, the animal may develop cancer within a few months of the induction of oncogene the expression. The animal may also be treated with carcinogens, e.g., 9,10-dimethyl-1,2-benzanthracene or ENU, to expedite this process.

The chimeric animal models of this invention provide flexibility in developing models of different diseases. For example, ES cell lines may be established for different cancer models by knocking out a tumor suppressor gene (e.g., p53) and introducing a reporter gene (e.g., luciferase), a tissue-specific reverse tetracycline transactivator gene (i.e., MMTV-rtTA) and an oncogene of choice (e.g., Akt, Her2V664E, Her2, Bcl2, K-Ras and Cyclin D1) under the control of a promoter regulated by reverse tetracycline transactivator (rtTA). These cancer models allow the comparison study of cancers of different etiology, and comparison study of different oncogenes in cancer development.

III. Exemplary Uses

The chimeric animals of this invention and diseased cells derived from the animals can be used to delineate the initiation, progression, maintenance, regression, minimal residual disease, recurrence, or any other developmental stages of a specific disease such as a cancer. They can also be used for drug target identification, target validation, and efficacy testing during drug development.

A. Identification of New Cancer Related Genes

The chimeric cancer models of this invention can be used to examine the oncogenicity of any gene, and to identify new cancer related genes. For instance, a candidate oncogene and a null mutation of an endogenous tumor suppressor gene (or an RNAi construct targeting the tumor suppressor gene) may be co-introduced into ES cells. A higher incidence rate, or shorter latency, of cancer originating from the ES cells in a resulting chimeric animal, as compared to that originating from ES cells containing only the null mutation in a control animal, indicates that the candidate gene is an oncogene.

In addition, a gene expression profile for a chimeric animal having cancer due to the expression of an introduced oncogene via ES cells can be established. Then, comparisons of gene expression profiles at different stages of cancer development can be performed to identify genes whose expression patterns are altered. Techniques used to establish gene expression profiles include the use of suppression subtraction (in cell culture), differential display, proteomic analysis, serial analysis of gene expression (SAGE) and comparative genomic hybridization (CGH). To allow high throughput profiling, cDNA and/or oligonucleotide microarrays can be used.

Gene expression profiles in separate animal models that contain different genetic alterations predisposing them to the same type of cancer can be compared to identify tumor-related genes. As discussed below, surrogate biomarkers. For instance, overexpression of any one of Akt, Her2, Bcl-2, K-ras and cycline D1, or activating mutations of any of these genes (e.g., Her2V664E) can cause breast cancer. By comparing gene expression profiles in breast cancer tissues isolated from different chimeric animals each containing mutations in one of these genes, one can obtain information as to the different pathways involved in the development (including initiation, maintenance and regression) of breast cancer. This information will be valuable in determining therapeutic regimen for breast cancer caused by different genetic lesions.

B. Identification of Surrogate Biomarkers

The chimeric animals of the invention also can be used to identify surrogate biomarkers for diagnosis or to follow disease progression in a nonhuman animal (e.g., a mouse, a rat, or a nonhuman primate). The biomarkers can be identified based on the differences between the expression profiles for a chimeric animal that has developed a disease and one that has not developed the disease. Blood, urine or other body fluids from the animals can be tested with ELISAs or other assays to determine which biomarkers are released from the diseased tissue into circulation during genesis, maintenance, progression or regression of the disease. Such diagnosis may involve detecting the expression or activity level of the biomarker, wherein an abnormally high level relative to control (e.g., at least about 50%, 100%, 150%, 200%, 250%, or 300% higher) is indicative of an abnormal condition. These biomarkers are particularly useful clinically in following disease progression post disease therapy. These biomarkers can also be used clinically to assess the toxicity of any disease therapy.

C. Identification of Therapeutic Agents

The chimeric animals of the invention can be used to screen therapeutic agents to treat a disease. One such method involves administering a candidate compound to an animal that has developed a cancer. Then one can observe the effect of the compound, if any, on the cancer. One can measure, e.g., tumor size, metastasis, or angiogenesis. Alternatively, one can observe the effect of the compound on the expression or activity level of a biomarker for the cancer.

D. Identification of Genes Crucial for Organ Survival or Function

To identify a gene crucial for organ survival or function, one can evaluate regeneration in an organ containing cells having a genetic alteration in a candidate gene. A genetic alteration of a candidate gene can be introduced into an ES cell line so that the expression of the candidate gene is inhibited or stimulated through an inducible mechanism. In a resulting chimeric animal, the expression of the candidate gene in the chimeric cells may be induced by an inducer molecule or inhibited by RNA interference. Upon induction or inhibition, the degree of chimerism may change in the organ. For example, the percentage of chimeric cells may change in a liver after induction of the expression of a candidate gene. If loss or overexpression of the candidate gene product is detrimental to liver cell survival, chimeric cells will die upon induction, and the chimerism in the liver will decrease.

E. Study of Differentiation Potential of ES Cells

In some embodiments, one can study differentiation potential, of such ES cells in vivo in the context of tumorigenesis. A chimeric animal having cells that originate from ES cells containing certain genetic alterations may be more prone to develop tumors in certain tissues. A comparison of tumor development in different tissues of the chimeric animals will thus provide insight into which genetic alterations preferentially cause tumors in which tissues.

F. Study of Cell/Cell Interactions in Tumor Formation

The chimeric animals of the invention may be used to study the contribution of cell/cell interaction to tumor formation. The cell/cell interaction may involve cells having different genetic backgrounds that originate from ES cells having different genetic alterations, or from cells derived from two different sources, e.g., the introduced ES cells and the host blastocyst cells.

By way of example, the host blastocyst for ES cell injection is genetically modified to allow studies of stromal contribution to tumor development. The host blastocyst can be derived from, e.g., a transgenic animal that produces elevated levels of a growth factor or cytokine in a specific tissue; thus one can study the effect of this growth factor or cytokine on the development of tumors arising from cellular progeny of the introduced ES cells in that tissue. The host blastocyst can also be derived from, e.g., a transgenic animal that is deficient in a certain cellular product (e.g., an adhesion molecule, an angiogenesis factor, a receptor, or a signaling molecule) in a specific tissue; thus one can study the role of this cellular product in providing stromal support for tumor development in that tissue.

In another example, ES cells from two ES cell lines having different genetic alterations are co-introduced into blastocysts and the resulting chimeric animals may develop a tumor that originates from both ES cell lines. Tumor formation in such chimeric animals can be compared with chimeric animals containing tumor cells originating from only one of the two ES cell lines. Such a comparison will provide insight into the effect of interactions between cells having the different genetic alterations on tumor formation.

G. Study of Toxicity of a Genetic Element

The chimeric animals of this invention can be used to measure quantitatively the toxicity of a genetic element, e.g., a gene introduced into a cell (e.g., an inducible oncogene), an overexpressed endogenous gene, an RNAi construct against an endogenous gene (e.g., a tumor suppressor gene), a construct that knocks out an endogenous gene, etc. To do this, one can generate a chimeric animal from a host blastocyst that has been injected with ES cells containing the test genetic element, wherein the host blastocyst itself does not contain this test genetic element. He can then compare the chimerism of the animal with that of a control animal, e.g., a chimeric animal developed with control ES cells that do not contain the genetic element, or a chimeric animal developed with the same ES cells but the test genetic element in those cells or progeny thereof are not expressed (e.g., induced). A lower degree of chimerism indicates that the test genetic element affects development negatively. A higher degree of chimerism indicates the opposite.

A variety of methods can be used to determine the degree of chimerism. For instance, a biopsy of the organ can be obtained and analyzed by biochemical methods. Alternatively, the host embryo and the ES cell are engineered to express a different fluorescent protein (e.g., one of GFP, RFP, and YFP), and the ratio of the two fluorescent signals, which is indicative of chimerism, is analyzed by in vivo imaging.

H. Mammalian Second Site Suppressor (MaSS) Screen

The chimeric animals of this invention can be used in a MaSS screen to identify cancer-related genes. In general, a MaSS screen involves: (a) maintaining cells in which tumorigenicity depends on the expression of an inducible oncogene under conditions in which the expression of the oncogene is not induced; (b) introducing into the cells a nucleic acid molecule, e.g., a retrovirus, that integrates into the genomes of the cells, thereby tagging the loci at which it integrates; (c) identifying cells in which tumorigenicity has been induced by integration of the nucleic acid molecule; and (d) identifying genes that have been tagged by the integrated nucleic acid molecule. Methods and materials for performance of a MaSS screen are described in WO 02/079419.

IV. Examples

The invention is further illustrated by the following examples. The examples are provided for illustrative purposes only, and are not to be construed as limiting the scope or content of the invention in any way.

Example 1

HER2 Lung Cancer Model

The frequency of HER2/neu overexpression in lung cancer has mostly been studied in non-small cell lung cancer, and the reported frequencies of HER2/neu overexpression range from 5 to 59%. The patients with HER2/neu-positive tumors have significantly shorter survival. HER2/neu overexpression has also been shown to contribute to tumorigenesis in lung tumor cell lines. See, e.g., Hirsch et al., Lung Cancer 36:263-4 (2002); and Gatzemeier et al., Annals of Oncology 15:19-27 (2004). However, anti-HER2/neu antibodies (trastuzumab or HERCEPTIN®) do not seem efficacious in treating HER2-positive non-small cell lung cancer in humans. Gatzemeier et al., supra.

Chimeric mice that inducibly overexpress HER2/neu in their lungs and develop lung cancer shortly after induction were produced. These mice were used to show a cause-effect relationship between HER2/neu and lung cancer. Since a human HER2/neu coding sequence was used in making the mice, the mice are useful for, inter alia, developing lung cancer therapeutics that target HER2/neu in human patients and for testing the anti-lung cancer efficacy of known HER2/neu drugs. The mice were made as follows.

An INK4a−/− ES cell line was first co-transfected with two expression constructs. The first construct (CCSP-rtTA) contained a reverse tetracycline transactivator (rtTA) coding sequence linked operably to a Clara cell secretory protein (CCSP) promoter (Fisher et al., Genes & Development 15:3249-62 (2001)). The second construct (TetO-luc) contained a luciferase (luc) coding sequence linked operably to a minimal-fos promoter containing a tetracycline operator sequence (TetO). ES cell lines containing both CCSP-rtTA and TetO-luc were established by co-transfection of these two constructs together with PGK-puromycin. Puromycin resistant cells were clonally isolated and genotyped by PCR and Southern Blot for the presence of both CCSP-rtTA and TetOLuc. Fifteen of these resultant cell lines were injected into blastocysts to generate chimeric mice, to assess the relative performance of the cell lines. Inducibility of the luciferase reporter gene in the lung was studied in vitro by comparison of luminescent signals of lung samples dissected from chimeras that had or had not been exposed to doxycycline.

Two of the cell lines that passed the inducibility analysis were further transfected with a third construct containing a human HER2/neu coding sequence linked operably to TetO. The HER2/neu polypeptide product contained a V664E/Neu mutation (i.e., substitution of glutamic acid for valine at position 664) along with PGK-hygromycin 659). Thus, in a chimeric mouse containing cells descended from these engineered ES cells, the expression of the HER2/neu gene was under the control of the rtTA and tetracycline or a tetracycline analog (e.g., doxycycline). And since the rtTA was under the control of the lung-specific CCSP promoter, the HER/neu oncogene would be expressed inducibly only in the lungs.

Then, twelve of these ES cell lines were injected into mouse blastocysts from C57/BL6 females. The injected blastocysts were transferred to surrogate mothers for gestation. As assessed qualitatively (by coat color), approximately 5% to greater than 90% of the resulting animals' body developed in mosaic fashion from the engineered ES cells. The mice were then given doxycycline-containing drinking water (2 mg/ml) at week four. The lung tissues from the chimeric mice were analyzed by RT-PCR and immunohistochemistry. Lung adenomas were observed within seven weeks after the treatment started. Within two to five months, invasive adenocarcinoma developed in the lungs. Thus, these data demonstrated that HER2/neu can initiate lung cancer.

The chimeric HER2/neu mice offered several advantages over conventional transgenic lung cancer models containing the same genetic modifications. In transgenic mice that inducibly expressed HER2/neu in the lungs, severe hyperplasia developed throughout the lungs within two to three weeks of induction. The lungs became nonfunctional, resulting in death before any tumor had a chance to develop. Similarly, in transgenic mice that inducibly expressed K-ras in the lungs (Fisher et al., supra), the tumor loads were so high that the animals died before the tumors had a chance to become invasive. In the chimeric HER2/neu mice, in contrast, there was enough healthy lung tissue left to support survival after hyperplasia developed. As a result, transformed lung cells had time to progress into more malignant, invasive tumors. Therefore, the chimeric mice allowed more detailed studies of tumor development.

Example 2

HER2 Breast Cancer Model

Ink4a homozygous null ES cells were co-transfected with the following four constructs, as separate fragments: MMTV-rtTA, TetO-Her2$^{V664\ Eneu}$, TetO-luciferase and PGK-puromycin. Puromycin-resistant cells were genotyped by PCR and Southern blot. Inducibility of the oncogenes in ES cells was analyzed by northern blot. The transfected ES cells were injected into C57BL/6 blastocysts, which were transplanted into pseudo-pregnant female mice for gestation leading to birth of the chimeric mice.

The mouse mammary tumor virus long terminal repeat (MMTV) is used to drive breast-specific expression of the reverse tetracycline transactivator (rtTA). The rtTA provides for breast-specific expression of the HER2 activated oncogene when doxycycline is provided to the mice, e.g., in their drinking water.

Inducibility of the HER2 oncogene and luciferase was confirmed by RT-PCR and luciferase assay (respectively), using cultured cells derived from the mouse. Mammary glands were removed from chimeric mice and digested with collagenase. Half of the organoids collected were cultured in the presence of doxycycline, and the other half was cultured without doxycycline. After five days in culture, the cells were trypsinized, and one tenth of the cells were used for luciferase assay, and the rest were used for RNA extraction.

The histology analysis of tumors harvested from HER2 breast cancer model mice showed invasive adenocarcinomas. Two major patterns were distinguished. They were a solid sheet growth pattern, and a nested growth pattern with necrotic centers.

Immunohistochemistry analysis of mammary tumors from HER2 breast cancer model mice revealed two cell types within the tumors. The first cell type was epithelial origin (cytokeratin positive), and showed HER2 expression and strong proliferation. The second cell type was mesenchymal origin with fibroblast-like appearance. These cells were collagen positive. These cells did not show strong proliferation, and they displayed stromal function. Apoptosis was seen in the necrotic centers of the epithelial part of the tumors.

Figure 2:
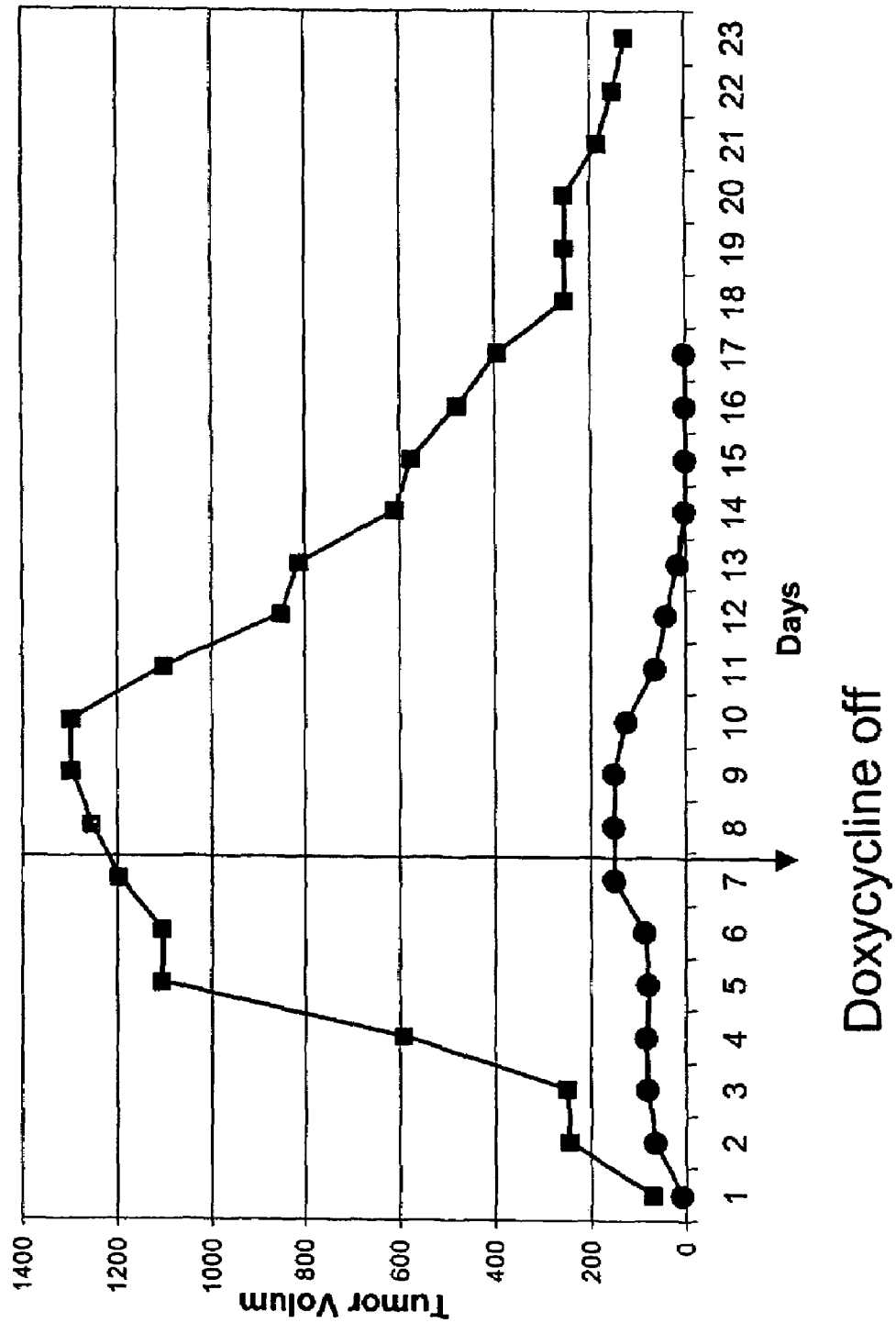
FIG. 2 is a graph of data showing the regression of two tumors from a breast Her2 model mouse (mouse #331) after doxycycline withdrawal from the drinking water. Squares represent the tumor that arose in the right fourth mammary gland. Circles represent the tumor that arose in the left fourth mammary gland. The mouse was on doxycycline for 7 weeks. Day 1 represents the first measurement of the tumors. On day 7, after measuring the tumor size, doxycycline was withdrawn from the water. Tumors were measured every day for 23 days. Doxycycline withdrawal resulted in the complete regression of one tumors and the near complete regression of the other tumor during the study period.

Tumor regression studies were performed using the HER2 breast cancer model mice. Two mice, each carrying more than two doxycycline-induced tumors, were selected. The tumor size of two tumors each was measured using calipers before and after doxycycline was withdrawn from the drinking water. Doxycycline was withdrawn at day six. Tumor size was measured daily. The tumor size measurements were used to calculate the tumor volume. Results were plotted and the regression of the tumors was determined. All tumors regressed, displaying doxycycline-dependence (FIGS. 1 and 2). Immunohistochemistry analysis of tumor regression confirmed doxycycline-dependent HER2 expression. Thus, growth and maintenance of the tumors were shown to depend on HER2 expression.

Example 3

K-RAS Breast Cancer Model

Ink4a homozygous null ES cells were co-transfected with the following four constructs, as separate fragments: MMTV-rtTA, TetO-K-RAS$^{G12V}$, TetO-luciferase and PGK-puromycin. Puromycin-resistant cells were genotyped by PCR and Southern blot. Inducibility of the oncogenes in ES cells was analyzed by northern blot. The transfected ES cells were injected into C57BL/6 blastocysts, which were transplanted into pseudo-pregnant female mice for gestation leading to birth of the chimeric mice.

Inducibility of the K-RAS oncogene and luciferase was confirmed by RT-PCR and luciferase assay (respectively), using cultured cells derived from the mouse. Mammary glands were removed from chimeric mice and digested with collagenase. Half of the organoids collected were cultured in the presence of doxycycline, and the other half was cultured without doxycycline. After five days in culture, the cells were trypsinized, and one tenth of the cells were used for luciferase assay, and the rest were used for RNA extraction.

The histology analysis of tumors harvested from K-RAS breast cancer model mice showed hyperplasia in the epithelial ducts of the mammary gland after 2 months on doxycycline. This hyperplasia is observed until the end of the observation period (6 month on doxycycline).

Example 4

K-RAS Lung Cancer Model

Ink4a homozygous null ES cells were co-transfected with the following four constructs, as separate fragments: CCSP-rtTA, TetO-K-RAS$^{G12V}$, TetO-luciferase and PGK-puromycin. Puromycin-resistant cells were genotyped by PCR and Southern blot. Inducibility of the oncogenes in ES cells was analyzed by northern blot. The transfected ES cells were injected into C57BL/6 blastocysts, which were transplanted into pseudo-pregnant female mice for gestation leading to birth of the chimeric mice.

Inducibility of the K-RAS oncogene and luciferase was confirmed by RT-PCR, Northern blot and luciferase assay (respectively), using tissue derived from the mouse lungs. Lungs were removed from chimeric mice and homogenized. Homogenized material from mice on and off Doxycycline was compared in Luciferase assays and RNA expression analysis.

The histological analysis of lungs from the mice on doxycycline revealed multiple adenocarcinomas in the lung. The adenocarcinomas can be seen as early as 3 month on doxycycline. Chimeras with a low percentage of ES-cells showed a longer latency for tumor development with an overall decreased tumor burden. The tumors derive from type II pneumocytes as analyzed by immunohistochemistry using antibodies against the SPC and CC10 antigens.

Other embodiments are within the following claims.

We claim:

1. A method of making a chimeric mouse cancer model, comprising:
   (a) providing a mouse ES cell whose genome comprises homozygous inactivation of an endogenous tumor suppressor gene;
   (b) transfecting the mouse ES cell with (i) a first vector comprising a recombinant oncogene operably linked to a tetracycline dependent inducible promoter, and (ii) a second vector comprising a tissue-specific reverse tetracycline transactivator gene;
   (c) injecting the mouse ES cell into a mouse blastocyst, and
   (d) transferring the blastocyst into a pseudo-pregnant female mouse for gestation leading to birth of the chimeric mouse; wherein induction of the oncogene following administration of tetracycline analog to said mouse results in the development of tumor.

2. The method of claim 1, wherein the recombinant oncogene is selected from the group consisting of K-RAS, H-RAS, N-RAS, EGFR, MDM2, RhoC, AKT1, AKT2, c-myc, n-myc, β-catenin, PDGF, C-MET, PI3K-CA, CDK4, cyclin B1, cyclin D1, estrogen receptor gene, progesterone receptor gene, Her2, ErbB1, ErbB3, ErbB4, TGF-α, TGF-β, ras-GAP, Shc, Nck, Src, Yes, Fyn, Wnt, Bcl$_2$, PyV MT, and SV40 LT.

3. The method of claim 2, wherein the recombinant oncogene is HER2, K-RAS or EGFR.

4. The method of claim 1, wherein the tumor suppressor gene is selected from the group consisting of Rb, P53, INK4a, PTEN, LATS, Apafl, Caspase 8, APC, DPC4, KLF6, GSTP1, ELAC2/HPC2 or NKX3.1, ATM, CHK2, ATR., BRCAI, BRCA2, MSH2, MSH6, PMS2, Ku70, Ku80, DNA/PK, XRCC4 or MLH 1, NF 1, NF2, APC, Adenomatous Polyposis Coli (APC), Wilms tumor-suppressor protein (WT), Patched and FHIT.

5. The method of claim 4, wherein the tumor suppressor gene is INK4a.

6. The method of claim 1, wherein the inducible promoter is a TetO promoter.

* * * * *